United States Patent [19]

Kern

[11] 4,436,999

[45] Mar. 13, 1984

[54] STRUCTURAL DEFECT DETECTION

[75] Inventor: Werner Kern, Hightstown, N.J.

[73] Assignee: RCA Corporation, New York, N.Y.

[21] Appl. No.: 386,240

[22] Filed: Jun. 8, 1982

[51] Int. Cl.³ ............................................ G01N 1/30
[52] U.S. Cl. .................................................. 250/302
[58] Field of Search ................. 250/302, 459.1, 484.1; 73/104

[56] References Cited

U.S. PATENT DOCUMENTS

| | | | |
|---|---|---|---|
| 3,530,045 | 9/1970 | Alburger | 204/1 |
| 3,652,224 | 3/1972 | Johnson et al. | 250/302 X |
| 4,039,838 | 8/1977 | DiPiazza | 250/483 |
| 4,125,440 | 11/1978 | Markovits | 204/1 T |
| 4,172,224 | 10/1979 | Lapinski et al. | 250/302 |
| 4,237,379 | 12/1980 | Deckert et al. | 250/302 |
| 4,278,508 | 7/1981 | White et al. | 204/1 T |

OTHER PUBLICATIONS

W. Kern et al., "Fluorescence Techniques Allow Defect Study in Microelectronics", *Industrial Research & Development*, May, 1982.

*Primary Examiner*—Alfred E. Smith
*Assistant Examiner*—Jack I. Berman
*Attorney, Agent, or Firm*—Birgit E. Morris; R. Hain Swope

[57] ABSTRACT

A method and composition for the detection of microdefects in the surface layer of a substrate is disclosed. The composition utilizes dimethylsulfoxide as a primary solvent and a fluorescent organic compound which fluoresces principally in solution. The visibility of microdefects is enhanced by etching the substrate underlying them to form channels for the fluorescent compound.

7 Claims, 4 Drawing Figures

STRUCTURAL DEFECT DETECTION

This invention relates to the detection of localized structural defects in solids, particularly insulator coatings on semiconductor devices, utilizing fluorescing organic compounds.

BACKGROUND OF THE INVENTION

The detection and study of corrosion of small metal and insulator structures is important economically in the processing and reliability of semiconductors and similar devices. The use of fluorescent compounds for such use, as a general matter, is known. U.S. Pat. No. 4,039,838, for example, discloses the use of an amorphous coating of a fluorescent compound on a substrate transparent to visible light to examine photomasks by ultraviolet light.

U.S. Pat. No. 3,530,045 discloses the use of layers of stiff gel containing a color indicator and a conductive liquid to detect defects in conductive test parts. In this method, the color indicator gel is interposed between the test piece and the conductive liquid-containing gel, which function as oppositely charged electrodes when an electrical current is passed therethrough.

U.S. Pat. No. 4,278,508 discloses the use of a pH sensitive fluorescent compound to detect a cathodic corrosion site in a metallic surface of the substrate. The dye is coated on the metallic surface and an electrical bias is applied thereto. The surface is then exposed to ultraviolet light whereupon the corrosion sites fluoresce. U.S. Pat. No. 4,237,379 discloses a means of testing the quality of a protective layer in devices, such as integrated circuit devices, by applying a fluorescein-containing compound thereto and exposing to UV irradiation while applying a voltage between two conductors.

Improvements in the use of fluroescent compounds to detect microdefects in the surface layer of, e.g., semiconductor devices, are provided in accordance with this invention.

SUMMARY OF THE INVENTION

In accordance with this invention, solutions of fluorescent compounds in dimethyl sulfoxide are provided which are advantageous in the detection of microdefects in, e.g., semiconductor devices. The fluorescent compounds utilized are characterized by fluorescing only in solution. The use of such compositions in combination with an etching step provides an enhanced viewing of the defects to be detected.

DETAILED DESCRIPTION OF THE INVENTION

Figure 1:
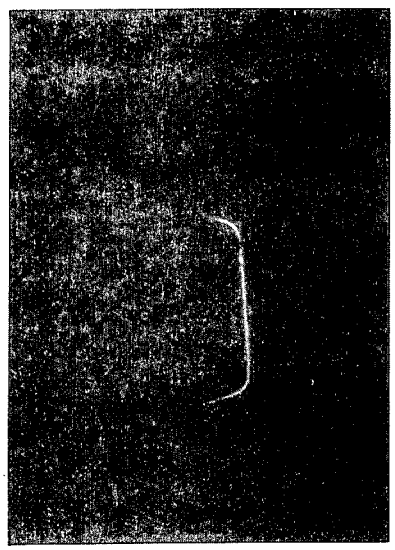
FIGS. 1 and 2 are photomicrographs of microdefects in the insulator coating of a device which has been demarcated in accordance with this invention.

The electrophoretic decorating methodology and compositions known heretofore, e.g., U.S. Pat. Nos. 3,530,045, 4,237,379 and 4,278,508, are effective for detecting insulator defects. Such methods, however, require the application of an external potential which may be extremely difficult, if not impossible, if one wishes to test a single chip, or when a substrate has no conductive parts. Their usefulness for detecting microdefects, therefore, is, at best, limited.

Microdefects, as used herein, particularly with reference to insulator coatings, refers to cracks and pinholes which form, in effect, microcavities with a depth up to the thickness of the layer, typically several thousand angstroms to several micrometers. I have found that by optimizing the fluorescing compound, the solvent system therefore and the technique for its application, a sharp demarcation of such defects can be achieved.

The fluorescent organic compounds utilized in this invention are, of course, selected based on the conventional requirements of fluorescent color and intensity, solubility and chemical stability. In addition, it is essential that the fluorescent compounds of this invention have little or no fluorescence in the dry state. Although relatively few in number, such compounds are known. Preferred among this group of compounds are green fluorescing fluorescein sodium and esculine monohydrate, $\beta$-methylumbelliferone which fluoresces bright blue, and 5-(p-dimethylaminobenzylidene)-rhodanine, which fluoresces yellow-green to blue. Other compounds having similar properties such as acridine orange, eosine-Y and sulfuric acid-containing solutions of quinine monohydrate have been tried, but were unacceptable for a number of reasons. For example, the latter solution fades rapidly and irreversibly in ultraviolet light.

In accordance with this invention, the surface of the sample is brought into contact with a solution of the fluorescent compound for a time sufficient for the solution to penetrate into the microdefects in the surface. Generally, at least 2 minutes is required with about 5 to 10 minutes being preferred. The substrate may, for example, be immersed in the solution. The excess solution is then drained from the surface and the surface is allowed to dry. The substrate can be examined under a fluorescence microscope when the surface becomes semi-dry. Alternatively, the sample can be covered with a thin microscope cover glass and later examined. In either case, the effect is essentially the same, i.e. the fluorescing solution remains intact in the microdefect while the surface of the sample is dry or semi-dry. It will be appreciated that it is necessary to irradiate the substrate with actinic radiation, typically violet-blue or ultraviolet light, while the fluorescent compound in the microcracks remains in solution. By utilizing compounds which fluoresce only in solution, the microdefects are thus brilliantly visible against a black background.

The fluorescent organic compounds of this invention are preferably applied to the sample in a solution based on dimethyl sulfoxide (DMSO). The properties of DMSO which make it ideally suited for detecting microdefects in accordance with this invention are very low volatility, low vapor pressure, good miscibility with water and organic solvents such as ethanol, and strong solvent capabilities. In addition to DMSO, the subject compositions contain a suitable lower alkanol such as ethanol, a suitable surfactant and water. By "suitable" is meant an ingredient which is compatible with the fluorescent organic compound and the remaining ingredients under the contemplated conditions of use for the subject compositions.

In general, the fluorescent compositions of this invention contain from about 0.005 to about 0.05, preferably about 0.02, percent weight to volume of the fluorescent compound, from about 0.05 to about 0.5, preferably about 0.2, percent weight to volume of the surfactant and, on a volume to volume basis, are comprised of about 25 to about 75, preferably about 50, percent of DMSO, from about 20 to about 60, preferably about 40, percent of the lower alkanol and the remainder water. The lower alkanol and surfactant are present to enhance wetting and penetration. Suitable surfactants include, for example, FC-93 available from 3-M Company, Minneapolis, Minn., and certain of the Tergitol series of surfactants available from Union Carbide Corp. The compositions of this invention further contain a sufficient amount of a suitable base to adjust the pH to a level necessary for optimum fluorescence. Generally, an inorganic base such as, e.g., potassium hydroxide, is utilized.

The solution compositions of this invention are advantageous in that, although the excess may be readily drained from the surface of the sample, they remain in deep defects for a long time without drying out. In addition, they dry without leaving a sticky residue which is a characteristic disadvantage of solutions containing a viscous, nonvolatile substance such as glycerol. Such substances have been used heretofore to prevent or retard solutions of fluorescent compounds from drying out on the surface of the sample.

In contrast, it is contemplated herein that the subject fluorescent solutions readily drain from the surface and remain intact in the defect cavity after the surface has dried. Thus, even microdefects are clearly demarcated because the compositions and methodology of this invention allow them to be made visible against a black background. Even with the improved compositions of this invention, however, it may be difficult to demarcate minute cracks in insulator films. A method is provided herein whereby even cracks of less than one thousand angstroms wide may be clearly rendered visible.

In accordance with this invention, a sample to be tested for microdefects is initially treated with an etchant composition which etches the underlying substrate, but does not etch the top layer. The etchant solution penetrates the microcracks and etches the substrate underneath isotropically to form a channel. The etchant is then removed by thorough rinsing of the sample. The sample is then dried and the subject fluorescent compositions applied thereto.

Figure 2:
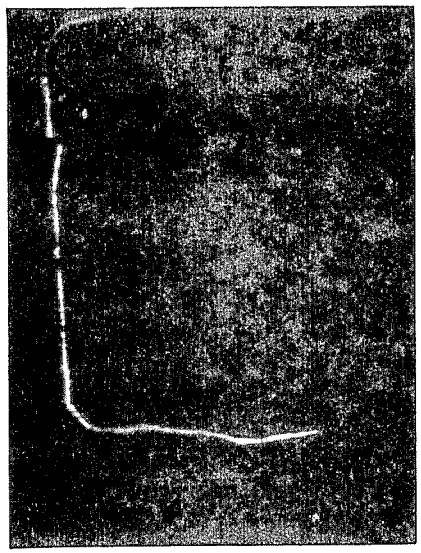
Figure 3:
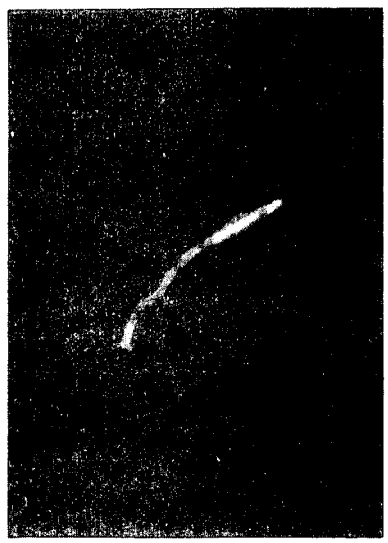
FIGS. 3 and 4 are photomicrographs of the devices of the type shown in FIGS. 1 and 2 wherein the substrate has been selectively etched prior to demarcation of the defects.
Figure 4:

The process of etching the substrate prior to utilizing the dye compositions of this invention will produce a substantial increase in the visibility of the microdefect. For example, the visibility of a crack 1000 angstroms wide can be increased 10 fold to 1.0 micrometer by this technique which would etch approximately 4500 angstroms into the substrate. An illustration of this effect can be seen in the FIGURES. FIGS. 1 and 2 are photomicrographs of microdefects in different areas of a 1.7-micrometer thick glass film on aluminum demarcated with esculine monohydrate. The average width of the microdefects is about 3000 angstroms. In FIGS. 3 and 4, similar substrate samples were treated with a conventional aluminum etchant solution comprising a mixture of phosphoric, nitric and acetic acids which was applied to the substrate at about 50° C. for one minute. The substrate was rinsed thoroughly to remove the etchant, dried, and the fluorescent solution applied thereto. The difference in visibility of the microdefects is striking. The original microdefect cracks can be seen in some instances appearing as a bright line against the fluorescing channel. The relative size of the channel clearly indicates the enhancing capability of the technique of this invention.

In the method of this invention, any suitable conventional etchant can be utilized to etch the substrate underlying a coating to be tested for microdefects. The important criterion in the selection of an etchant is that the coating to be tested must be completely impervious thereto. It is also essential that care be taken to thoroughly remove the etchant and the rinse solution to prevent any adverse reaction or effect on the subject fluorescent solution compositions.

The following Examples further illustrate this invention, it being understood that the invention is in no way intended to be limited to the details described therein. In the Examples, all parts and percentages are on a weight basis and all temperatures are in degrees Celsius, unless otherwise stated.

EXAMPLE 1

The fluorescent solution utilized in this experiment contained 0.02 percent weight to volume esculine monohydrate and, on a volume to volume basis, 50 percent of dimethylsulfoxide, 40 percent of ethanol, 9 percent of water, and 0.2 percent FC-93, a surfactant available from 3-M Company, Minneapolis, Minn. A sufficient amount, i.e. about 0.3 percent, of a 10 percent weight to volume aqueous solution of potassium hydroxide was added to adjust the pH to between 9 and 10. The solution was prepared by dissolving the esculine monohydrate in the dimethylsulfoxide and adding the remaining ingredients thereto. The solution was stable for several hours after which it was checked periodically and the pH adjusted to between 9 and 10 by the addition of potassium hydroxide.

Samples of aluminum-metallized integrated circuit wafer substrates having a 1.7-micrometer thick film of chemically vapor deposited $SiO_2$ glass were submerged in the fluorescent solution for 10 minutes. The samples were withdrawn from the solution and the excess removed by draining edgewise on lint-free filter paper. The samples dried evenly without a sticky residue. When the samples became semi-dry, they were observed under a fluorescence microscope. In order to demonstrate the stability of the solution in the defects, the samples were stored in air at 23° for three days. Photomicrographs were then made under a fluorescence microscope at 536 magnification. As is evident from FIGS. 1 and 2, microcracks have been clearly demarcated by this solution. The width of these cracks is about 0.3 micrometers.

EXAMPLE 2

Samples of the glass coated integrated circuit wafers utilized in Example 1 were immersed in a conventional aluminum etchant solution of, on a volume basis, 60 parts of 85 percent phosphoric acid, 12 parts of 99.7 percent acetic acid, 4 parts of distilled water, 1 part of 70 percent nitric acid and 0.43 part of FC-93 surfactant for one minute. The samples were removed from the etchant solution and thoroughly rinsed in deionized water. The samples were then treated with the fluorescent solution of Example 1 in the manner described and stored for three days. Photomicrographs were then taken as in Example 1. As is evident from FIGS. 3 and 4, a substantial defect enlargement, i.e. to a width of about 1.8 micrometer, is realized by this procedure. Some of the solution in the channels dried during the extended periods of illumination required for photographing the samples. This is evident from the central area of the channel demarcated in FIG. 4.

I claim:

1. A method of detecting microdefects in the surface layer of a substrate having two or more layers comprising:
   (a) contacting the surface of the substrate with a composition comprising a fluorescent organic compound characterized by the capacity to fluoresce only in solution, dimethyl sulfoxide, a suitable lower alkanol, a suitable surfactant and water for a time sufficient for the composition to penetrate the microdefects;
   (b) draining the excess composition from the surface of the substrate;
   (c) allowing the surface to dry;
   (d) irradiating the substrate while the dye in the microdefects remains in solution with actinic radiation, whereby fluorescence is activated only in the microdefects.

2. A method in accordance with claim 1, wherein the fluorescent organic compound is selected from the group consisting of esculine monohydrate, fluorescein sodium, B-methylumbelliferone and 5-(p-dimethylaminobenzylidene)rhodanine.

3. A method in accordance with claim 1, wherein the actinic radiation is ultraviolet or blue-violet light.

4. A method in accordance with claim 1, wherein the composition additionally contains a sufficient amount of a suitable base so that the pH of the composition is the optimum pH for maximum fluorescence of the fluorescent organic compound.

5. A method in accordance with claim 4 wherein the fluorescent organic compound is esculine monohydrate and the composition contains a sufficient amount of base so that the pH is between about 9 and 10.

6. A method in accordance with claim 1, wherein the method additionally includes, prior to step (a), the steps of contacting the substrate with an etchant composition which etches the layer immediately underlying the surface layer, but which will not etch the surface layer itself, thereby etching the underlying layer adjacent to any microdefects in the surface layer, and removing said etchant composition.

7. A method in accordance with claim 6, wherein the layer immediately underlying the surface layer is aluminum and the etching composition is a mixture of phosphoric acid, acetic acid, and nitric acid.

* * * * *